US011154853B2

(12) United States Patent
Gau et al.

(10) Patent No.: US 11,154,853 B2
(45) Date of Patent: Oct. 26, 2021

(54) GENERATION OF DATA FOR USE WITH ANTIMICROBIALS (71) Applicant: GeneFluidics, Inc., Irwindale, CA (US)

(72) Inventors: Jen-Jr Gau, Pasadena, CA (US); Michael Tomasek, Huntington Beach, CA (US)

(73) Assignee: GeneFluidics, Inc., Irwindale, CA (US)

( * ) Notice: Subject to any disclaimer, the term of this patent is extended or adjusted under 35 U.S.C. 154(b) by 0 days.

(21) Appl. No.: 16/231,135

(22) Filed: Dec. 21, 2018

(65) Prior Publication Data

US 2019/0134622 A1  May 9, 2019

Related U.S. Application Data (60) Division of application No. 15/582,725, filed on Apr. 30, 2017, and a continuation of application No. PCT/US2017/030318, filed on Apr. 30, 2017.

(51) Int. Cl.
*B01J 47/12* (2017.01)
*G16H 10/40* (2018.01)
*G16H 20/10* (2018.01)
*B01J 41/00* (2006.01)
*C07C 231/24* (2006.01)
*C12Q 1/04* (2006.01)
*C12Q 1/06* (2006.01)
*C12Q 1/18* (2006.01)

(52) U.S. Cl.
CPC ............ *B01J 47/12* (2013.01); *B01J 41/00* (2013.01); *C07C 231/24* (2013.01); *C12Q 1/04* (2013.01); *C12Q 1/06* (2013.01); *C12Q 1/18* (2013.01); *G16H 10/40* (2018.01); *G16H 20/10* (2018.01)

(58) Field of Classification Search
CPC ......... B01J 41/00; B01J 47/12; C07C 231/24; C12Q 1/04; C12Q 1/06; C12Q 1/18; C12Q 1/689; C12Q 2600/106; C12Q 1/025; C12Q 1/6806; C12Q 1/6841; C12Q 1/045; C12Q 1/08; C12Q 1/14; C12Q 1/68; C12Q 1/6893; C12Q 1/70; C12Q 2563/107; C12Q 2600/158; G16H 10/40; G16H 20/10; G01N 2021/6419; G01N 2035/00346; G01N 2035/1032; G01N 21/6458; G01N 35/025; G01N 35/1002; G01N 1/38; G01N 15/06; G01N 2015/0693; G01N 2035/0443; G01N 2035/0444; G01N 2035/0446; G01N 2035/0455; G01N 2035/00158; G01N 21/35; G01N 21/3577; G01N 21/3581; G01N 21/47; G01N 21/64; G01N 21/65; G01N 33/6848; G01N 35/00069; G01N 1/31; G01N 2001/302; G01N 2021/6441; G01N 21/6428; G01N 21/6456; G01N 2415/00; G01N 2500/10; G01N 27/125; G01N 27/301; G01N 27/302; G01N 27/4167; G01N 27/4168; G01N 33/521; G01N 33/542; G01N 33/5438; G02B 7/28; B01L 2300/0893; B01L 3/527; B01L 3/545; B01L 2300/042; B01L 2300/0645; B01L 2300/0681; B01L 2300/0829; B01L 2300/161; B01L 2300/165; B01L 3/5023; C12M 33/00; C12M 41/30; C12M 41/36; C12M 1/34; C12M 33/14; C12M 41/06; C12M 41/48; Y02A 90/10; Y02A 50/30; A61K 31/407; A61K 31/546; C12N 1/06; G16B 40/10

See application file for complete search history.

(56) References Cited

U.S. PATENT DOCUMENTS

| | | |
|---|---|---|
| 9,103,788 B2 | 8/2015 | Wilkes et al. |
| 2007/0196818 A1 | 8/2007 | O'Hara |
| 2011/0008791 A1 | 1/2011 | Rothman et al. |
| 2011/0256612 A1 | 10/2011 | Wechter |
| 2011/0262556 A1 | 10/2011 | Holladay et al. |
| 2016/0146810 A1 | 5/2016 | Cartwright et al. |
| 2018/0136204 A1 | 5/2018 | Weidemaier et al. |

FOREIGN PATENT DOCUMENTS

| | | |
|---|---|---|
| WO | 2013/130875 A1 | 9/2013 |
| WO | 2015/164225 A1 | 10/2015 |
| WO | 2015/189390 A1 | 12/2015 |
| WO | 2018203868 A1 | 11/2018 |

OTHER PUBLICATIONS

Copenheaver, Blaine R., International Search Report and Written Opinion, PCT/US2017/030318, dated Jul. 19, 2017.
Thomas, Shane, International Search Report and Written Opinion, PCT/US2019/046812, United States Patent and Trademark Office, dated Nov. 13, 2019.

(Continued)

*Primary Examiner* — Deborah K Ware (74) *Attorney, Agent, or Firm* — Gavrilovich, Dodd & Lindsey, LLP (57) ABSTRACT

An assay is performed so as to identify a pathogen in a sample taken from a patient. The identity of the pathogen in the patient sample is used to select an antimicrobial for treatment of the patient. The antimicrobial can be selected in less than 7 hours after the patient sample is taken from the patient. For instance, when the sample is blood, the antimicrobial can be selected in less than 7 hours after the patient sample is taken from the patient. When the sample is urine, the antimicrobial can be selected in less than 4 hours after the patient sample is taken from the patient.

15 Claims, 4 Drawing Sheets

(56) References Cited

OTHER PUBLICATIONS

Wittmann-Regis, Agnes, International Preliminary Report on Patentability and Written Opinion, PCT/US2017/030318, The International Bureau of WIPO, dated Nov. 14, 2019.
Karasinski et al., "Detection and identification of bacteria using antibiotic susceptibility and a multi-array electrochemical sensor with pattern recognition", Biosensors and Bioelectronics, 22, 2007, pp. 2643-2649.
Landre, Julien, Extended European Search Report, Application No. 17908721.8, European Patent Office, dated Oct. 19, 2020.
Nakamura, N. et al., "Electrochemical Detection of Viable Bacteria in Urine and Antibiotic Selection, Biosensors in Urine and Antibiotic Selection", Biosensors and Bioelectronics,vol. 6, No. 7, Jan. 1, 1991, pp. 575-580.

Figure 1

| dose (mg) | concentration (CFU/mL) | sex (M/F) | weight (Lbs.) | age (years) |
|---|---|---|---|---|
| 10 | ### | ### | ### - ### | ### |
| 10 | ### | ### | ### - ### | ### |
| 20 | ### | ### | ### - ### | ### |
| 20 | ### | ### | ### - ### | ### |
| 30 | ### | ### | ### - ### | ### |

GENERATION OF DATA FOR USE WITH ANTIMICROBIALS

RELATED APPLICATIONS

This application is a Divisional of U.S. patent application Ser. No. 12/582,725, filed on Apr. 30, 2017, entitled "Generation of Data for Use with Antimicrobials;" and this application is a continuation of International Patent Application Number PCT/US2017/030318, filed on Apr. 30, 2017, entitled "Generation of Data for Use with Antimicrobials;" each of which is incorporated herein in its entirety.

FIELD

The invention relates to generation of data and more particularly to use of data with antimicrobials.

BACKGROUND

Antimicrobials such as antibiotics are generally prescribed without the physician knowing the identity of the pathogen being treated or if a pathogen is even present. This practice has resulted in the overprescription of antibiotics that has led to antibiotic-resistant pathogens. This practice has likely developed as a result the long time (~48-72 hours) required for a physician to get lab results that indicate the presence and/or identity of pathogens when the physician is facing patients that want rapid treatments. This practice may also have developed due to the costs of identifying the pathogen exceeding the cost of treating with antimicrobials.

Another source of drug resistant pathogens is prescribing the incorrect dosage of antimicrobials to patients. For instance, the pathogen can develop resistance to the antimicrobial when the dosage is undesirably low. Undesirably high dosages of an antimicrobial can be harmful to organs such as the liver.

For the above reasons, there is a need for improvements in the use of antimicrobial data.

SUMMARY

In some instances, an assay is performed so as to identify a pathogen in a sample taken from a patient. The identity of the pathogen in the patient sample is used to select an antimicrobial for treatment of the patient. The antimicrobial can be selected in less than 7 hours after the patient sample is taken from the patient. For instance, when the sample is blood, the antimicrobial can be selected in less than 7 hours after the patient sample is taken from the patient. When the sample is urine, the antimicrobial can be selected in less than 4 hours after the patient sample is taken from the patient. In some instances, the antimicrobial is selected in less than 90 minutes after the patient sample is taken from the patient.

In some instances, a culture of a patient sample is performed while the patient sample is exposed to an antimicrobial candidate. The antimicrobial candidate is a candidate for treating a pathogen that is present in the patient sample. An assay is performed so as to identify a concentration of the pathogen in the culture. The identified concentration is used to characterize the susceptibility of the pathogen to the antimicrobial candidate. The susceptibility of the pathogen to the antimicrobial candidate is characterized in less than 90 minutes after the patient sample is taken from the patient.

In some instances, an assay is performed so as to identify a concentration of a pathogen in a patient sample. The patient sample is taken from the patient after the patient has received an antimicrobial at a dosage level selected to treat the pathogen. The dosage level is changed in response to comparing the identified concentration to dosage performance data. The identified concentration is compared to the dosage performance data in less than 90 minutes after the patient initially received the antimicrobial.

DESCRIPTION

The inventors have developed electrochemical sensors that can be used to assay samples for the presence and/or concentration of pathogens. Each assays is typically specific to a particular pathogen. As a result, when multiple pathogens are possible, multiple different assays can be performed with each of the assays being associated with one of the possible pathogens. If any of the assays indicates the presence of the pathogen, then pathogen(s) associated with those assays is/are present. As a result, the assays can identify the pathogen.

These assays have proven to have very low Limits Of Detection (LOD). For instance, in urine samples, these assays can have a LOD of 75,000 CFU/mL (Colony Forming Units/mL) without culturing to increase pathogen concentration. After 30 and 90 minutes of performing a viability culture on the sample, the LOD of same assay drops to 30,000 CFU/mL and 10,000 CFU/mL respectively. In whole blood, these assays can have a LOD of 2,000 (CFU/mL) without culturing to increase pathogen concentration. After 120 and 180 minutes of performing a viability culture on the whole blood sample, the LOD of the same assay drops to 35 CFU/mL and 1.0 CFU/mL respectively. As a result, little or no culturing time is needed in order to achieve accurate assay results even at low LOD levels. Further, these assays are easily performed in the same facilities where samples are taken from patients. Accordingly, the time associated with transporting samples to off-site facilities is also eliminated. Further, the amount of time needed to perform one of these assays on a sample is generally on the order of 30-240 minutes from the time the person(s) performing the assay receives the sample. Accordingly, it is possible to quickly receive the results of assays that are accurate at low LOD levels.

The ability of the electrochemical assays described above to quickly and accurately provides resulting indicating if a pathogen is present, the identity of pathogen(s) that are present, and the concentration of pathogen(s) that are present can revolutionize treatment with antimicrobials such as antibiotics, Cefepime, and Meropenem. For instance, knowing that a pathogen is not present can prevent the prescription of antimicrobials in situations when they are not effective. Additionally, knowing the identity of pathogen(s) that are present allows for the prescription of antimicrobials that are known to be effective against the pathogen(s). Further, the quick availability of these results permits these prescriptions to be made in a time period that is convenient for the patient. For instance, these prescriptions can often be made in time periods from fractions of an hour to several hours. As a result, these prescriptions can generally be made on the same day a sample is taken from the patient, while the patient is on the way home from the site where the sample was taken, or while the patient is still at the site where the sample was taken. Since antimicrobials will be tailored to the pathogens that are present, proliferation of antimicrobial-resistant pathogens can be reduced.

The ability to quickly know the concentration of the pathogen in a sample can further permit screening of antimicrobials before a prescription of an antimicrobial is made. For instance, the sample taken from a patient can be cultured in the presence of the antimicrobial(s) that are identified as being effective against the identified pathogen(s). In some instances, these cultures are performed using different concentrations of the identified antimicrobial(s). The same assay technologies can be used to measure the concentration of the pathogen in these cultures. These results can be compared to identify the antimicrobials and, in some instances, antimicrobial concentrations to which the pathogens are susceptible. The antimicrobial to which the pathogen is most susceptible can then be prescribed. Additionally or alternately, the dosage of the prescription can be a function of the effective antimicrobial concentration. For instance, when lower concentrations of an antimicrobial are shown to be effective against a pathogen, lower doses of the antimicrobial can be prescribed. When higher concentrations of an antimicrobial are shown to be effective against a pathogen, the prescribed dosage of the antimicrobial can be increased. As a result, the initial prescription given to a patient can be experimentally shown to be effective against the strain of pathogen expressed by the patient. The use of experimental results to tailor the prescription to the identified pathogen, the proliferation of antimicrobial-resistant pathogens can be further reduced.

The ability to quickly know the concentration of the pathogen in a sample can also revolutionize monitoring of patients after the initial prescription is administered to the patient. For instance, the dosage originally prescribed to a patient can be a function of the concentration of the pathogen in the sample (the initial concentration) and, in some instances, one or more secondary factors. After taking the first dose, one or more additional samples can be taken and the pathogen concentration (monitoring concentration) determined again. The first monitoring concentration(s) can be compared to dosage performance data that indicates the level of pathogen response that is desired for the prescribed antimicrobial. For instance, dosage performance data can indicate the level of pathogen concentration that should be present in the monitoring concentration(s) when the correct antimicrobial dosage is prescribed. The dosage can be adjusted or left alone in response the comparison. As a result, the overdosage and/or underdosage of the antimicrobial can be avoided. Avoidance of antimicrobial underdosing can reduce proliferation of treatment resistant pathogens. Avoidance of antimicrobial overdosing can reduce unnecessary stress to a patient's organs and systems.

The assays described above can be used in a pathogen characterization phase where the presence or absence of a pathogen in a sample taken from a patient is determined, any pathogen(s) in the sample are identified, and/or a concentration of any pathogen(s) in the sample is determined. A sample such as whole blood is taken from a patient (the patient sample). A series of processed samples are sequentially generated over time from the patient sample. The processed samples are tested so as to generate results that include one or more factors selected from the group consisting of whether a pathogen is present in the patient sample, the identity of a pathogen in the sample, and a concentration of the pathogen in the sample. The test of a processed sample can be an assay that is specific to a particular pathogen. As a result, the assay indicating that a pathogen is present in the processed sample also identifies the pathogen. When the assay that is specific to a particular pathogen and multiple different pathogens are suspected to be present in the patient sample, the series of tests described above can be repeated for multiple different assays that are each directed to a different one of the pathogens.

The tests are performed according to a testing schedule that lists a series of testing appointment times. The testing appointment times refer to a period of time for which a culture of the patient sample is performed. For instance, the patient sample is used to generate a culture sample that is cultured so as to increase the concentration of the pathogen(s) that is suspected to be present in the patient sample. In some instances, the patient sample is combined with a culture medium so as to generate the culture sample. In some instances, the culture medium and/or the culture sample is a liquid. For instance, the culture can be a liquid microbial culture.

At or near each of the testing appointment times, a portion of the culture sample is extracted and then used to generate a processed sample. The processed sample is suitable for use in subsequent assays. For instance, when the assays are to be performed using an electrochemical sensor, the processed sample can be suitable for use with the electrochemical sensor. As an example, the processed sample can be in direct physical contact with the electrochemical sensor and/or can be in direct physical contact with an electrode on the electrochemical sensor. In one example, the processed sample is a drop of liquid in contact with a working electrode on the electrochemical sensor. In some instances, each processed sample is formed by combining one or more reagents with an aliquot of the culture sample.

Since the processed samples are each generated at or near one of the testing appointment times, the testing appointment times indicates the period of time which the patient sample was cultured before being tested. For instance, a testing appointment time of 30 minutes indicates that the culture sample has been cultured for thirty minutes when the culture sample was used to generate one of the processed samples. In contrast, a testing appointment time of zero minutes indicates a processed sample that was generated concurrently with or shortly after starting the culture. As noted above, the culture is performed so as to increase the concentration of the pathogen(s) that is suspected to be present in the patient sample. Accordingly, the processed samples formed from culture samples taken at later testing appointment times would have higher concentrations of the one or more suspected pathogens increasing the opportunity for the assay to detect the presence of the pathogen.

A testing schedule can be a function of the patient sample type. For instance, when the patient sample is urine, the culture can be tested for the presence and/or concentration of the one or more suspected pathogens at testing appointment times of 0 minutes, 30 minutes, 60 minutes, 90 minutes. When the patient sample is whole blood, the culture can be tested for the presence and/or concentration pathogen at testing appointment times of 0 minutes, 120 minutes, and 180. The testing schedule can also be tuned in response to other variables such as the pathogen being tested, availability of technicians, availability of resources, and growth rate of pathogen being tested, and cost of testing.

If one of the tests for the presence and/or concentration of the one or more suspected pathogens shows that the pathogen is present in the culture, a positive result can be reported, additional tests can optionally be suspended and the culture can optionally be stopped. Additionally, an antimicrobial screening phase can be started as is described in more detail below. In addition to reporting the positive result, the concentration of pathogen in the patient sample can be reported and/or the identity of the one or more pathogens in the patient sample can be reported.

The culture time appointment for the last test on of the testing schedule serves as a culture time limit. As an example, when the patient sample is whole blood and the testing schedule has tests at culture times of 120 minutes and 180 minutes, the culture time of 180 minutes serves as the culture time limit. When the culture time limit is reached, the culture of the patient sample can optionally be stopped. If each of the tests in the testing schedule showed that the one or more suspected pathogens are not present in the culture, a negative result is reported.

Figure 1:
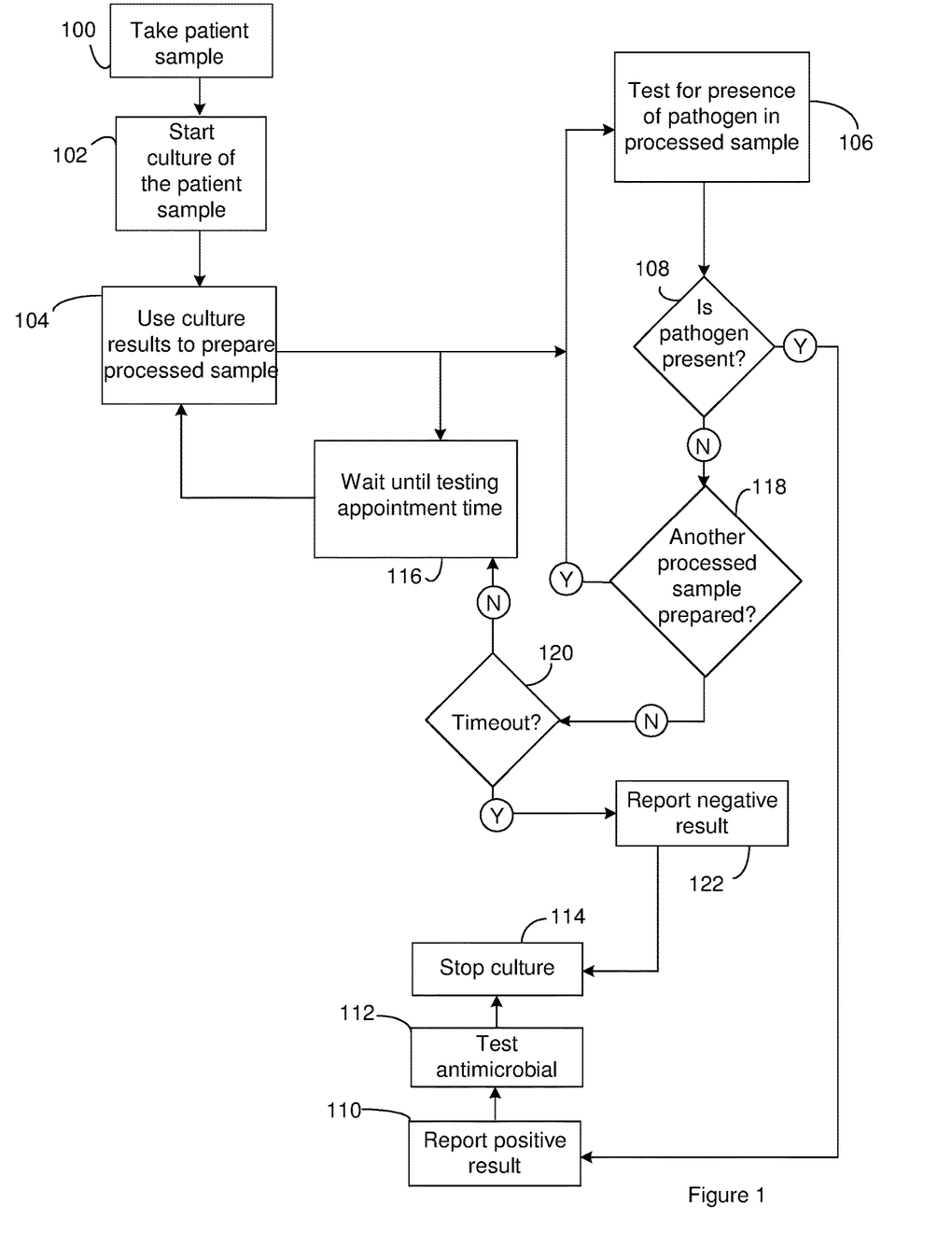
FIG. 1 a process flow for a pathogen characterization phase.

FIG. 1 illustrates an example of a process flow for a pathogen characterization phase. A patient sample is taken from the patient at process block 100. For instance, urine can be taken or blood can be taken. Before, during, or after taking of the sample, information can be gathered in order to identify one or more pathogens that are suspected to be responsible for the condition of the patient (suspected pathogens). For instance, the patient may be examined, interviewed, other people familiar with the patient can be interviewed and/or a medical history of the patient can be consulted. The process flow of FIG. 1 applies to a situation where a single pathogen is suspected. When multiple pathogens are suspected, a process flow according to FIG. 1 can be executed for each of the suspected pathogens. The different process flows can be executed in series and/or parallel.

A culture of the patient sample is started at process block 102. The culture can be performed so as to increase the concentration of suspected pathogen(s). In some instances, the patient sample is combined with a culture medium so as to provide a culture sample. In some instances, the culture medium and/or the culture sample is a liquid. For instance, the culture can be a liquid microbial culture. The culture time is measured from the start of the culture at process block 102. The culture time is considered to be zero minutes at the start of the culture. In general, a culture is considered to be started when the culture sample is heated. Accordingly, when a robotic system such as the Proteus is used to conduct the culture, the culture is considered to be started when the Proteus starts to heat the sample.

At process block 104, the culture sample is processed to as to generate a processed sample. The processed sample is suitable for use in subsequent assays. For instance, when the assays are to be performed using an electrochemical sensor, the processed sample can be suitable for use with the electrochemical sensor. As an example, the processed sample can be in direct physical contact with the electrochemical sensor and/or can be in direct physical contact with an electrode on the electrochemical sensor.

At process block 106, the processed sample is tested for the presence and/or concentration of one of the suspected pathogens. Testing can include an assay for determining the presence and/or concentration of the suspected pathogen. The assay can be performed with an electrochemical sensor. Accordingly, the assay can include cyclic voltammetry of the processed sample. As noted above, electrochemical assays may be specific to a particular pathogen. As a result, the assay is specific to the suspected pathogen. Since the test is performed shortly after starting the culturing of the patient sample, this assay can serve as the base test or the zero culture time test.

The results of the assay is reviewed to determine if the suspected pathogen is present in the processed sample (decision block 108). A positive result indicates that the suspected pathogen is present in the patient sample. Since the assay is associated with a particular pathogen, the identity of the pathogen that is present in the processed sample is known. The positive result is reported (process block 110), an antimicrobial screening phase can optionally be entered (process block 112), and the culture can optionally be stopped (process block 114). In addition to reporting the positive result, the concentration of pathogen in the patient sample can be reported and/or the identity of the one or more pathogens in the patient sample can be reported.

In addition to flow proceeding from process block 104 to process block 106, the flow also proceeds from process block 104 to process block 116. As noted above, culture samples are taken at one or more testing time appointments according to a testing schedule. At process block 116, the method waits until the next testing time appointment is reached. As each testing time appointment is reached, the culture sample is used to prepare a processed sample at process block 104. The repeated cycle provided by process block 104 and process block 116 results in a series of processed samples being generated at each of the testing time appointments.

When the suspected pathogen is not found at decision block 108 and another processed sample is ready for testing (decision block 118), the method flow returns to process block 106 and the processed sample is tested for the presence and/or concentration of the suspected pathogen. In situations where the method is returning to process block 106, the resulting test does not serve as the base test or the zero culture time test and the original base test or the zero culture time test continues to serve as the base test or the zero culture time test.

When the suspected pathogen is not found at decision block 108 and another processed sample has not been prepared for testing (decision block 118), the flow proceeds to decision block 120. At decision block 120, a determination is made whether the culture time currently exceeds the culture time limit or will exceed the culture time limit at the next testing appointment time. When the determination at decision block 120 is positive, a timeout has occurred and a negative result is reported at process block 122 and the culture can optionally be stopped at process block 114. When the determination at decision block 120 is negative, the flow has not timed out and the process flow returns to process block 116.

The assays in the above flow can be performed manually or using a robotic system such as the Proteus from GeneFluidics, Inc. of Irwindale, Ca., USA. A suitable electrochemical sensor for use in performing the above assays is the UtiMax sensor chip and/or the BsiMax ID/AST sensor chip sold by GeneFluidics, Inc. of Irwindale, Ca., USA. The assays can be performed by using these electrochemical sensors manually or with one of the robotics systems such as the Proteus Robotic System and/or the Lab Automation System sold by GeneFluidics, Inc. of Irwindale, Ca., USA. The reagents used in these assays can be purchased in reagent kits. For instance, a reagent kit for use with urinary tract infections is the UtiMax sold by GeneFluidics, Inc. of Irwindale, Ca., USA. Pathogens that can be identified with the UtiMax reagent kit include *E. coli, P. aeruginosa*, and *K. Pneumoniae* and more depending on the ID sensor chip configuration. The Limit of Detection (LOD) for an assay performed using the UtiMax reagent kit in combination with the Proteus system has been shown to be 75,000 CFU/mL without culturing to increase pathogen concentration. After 30 and 90 minutes of culturing, the same assay has been shown to have LODs of 30,000 CFU/mL and 10,000 CFU/mL respectively. A reagent kit for use with bloodstream infections is the BsiMax sold by GeneFluidics, Inc. of Irwindale, Ca. Pathogens that can be identified with the BsiMax reagent kit include *E. coli, P. aeruginosa*, and *S. aureus* and more depending on the ID sensor chip configuration. The Limit of Detection (LOD) for an assay performed using the BsiMax reagent kit in combination with the Proteus system has been shown to be 2,000 (CFU/mL) without culturing to increase pathogen concentration. After 120 and 180 minutes of culturing, the same assay has been shown to have LODs of 35 CFU/mL and 1.0 CFU/mL respectively. These LOD numbers are determined according to Clinical and Laboratory Standards Institute (CLSI) I document EP17-A, "Evaluation of Detection Capability for Clinical Laboratory Measurement Procedures." The UtiMax and the BsiMax reagent kits come with electrochemical sensors that can be used manually or with a robotic system such as the Proteus from GeneFluidics, Inc. of Irwindale, Ca., USA.

When an assay is performed manually, the patient sample and one or more reagents can be pipetted onto the electrochemical sensor. When an assay is performed with a robotic system such as the Proteus, the operator transports the patient sample into the designated reagent rack along with the vials containing reagents from the UtiMax or BsiMax reagent kits. The Proteus robotic system then processes the sample and transfers the processed sample onto the electrochemical sensors. In some instances, the Proteus robotic system adds one or more reagents to the processed sample on the sensor in order to form the processed sample. When the Proteus robotic system does not add any more reagents to the processed sample, the processed sample serves as the processed sample. The Proteus robotic system then tests the processed sample. For instance, the Proteus robotic system performs cyclic voltammetry on the processed sample. The Proteus robotic system provides the results to the operator. For instance, the Proteus robotic system can indicate to an operator the pathogen species identified by the system based on the sensor chip used for testing. It can also indicate if multiple pathogens have been detected and, can often identify each of the species detected. Additionally, if the pathogen species is not identified by one of the species-specific sensors, it can indicate whether the tested sample contains a Gram-negative or Gram-positive sample. The Proteus will also indicate whether the universal sensor that will detect any bacteria has produced a signal.

When using a robotic system such as the Proteus is used to perform an assay, the testing time period from the operator receiving the patient sample to receiving the results of the assay (an indication or positive or negative and/or concentration of pathogen) is generally on the order of 30-240 minutes. When manually performing an assay, the testing time period from the operator receiving the patient sample to receiving the results of the assay (an indication or positive or negative and/or concentration of pathogen) is generally on the order of 30-240 minutes. Accordingly, the assays described above can be performed in a testing time period greater than 30 minutes, 60 minutes, or 120 minutes and/or less than 3 hours, 4 hours, or 5 hours.

As is evident from FIG. 1, when pathogen is present in the patient sample, it is possible to get results of the pathogen characterization phase in short periods of time such as the time needed to take a patient sample and then prepare and test a processed sample. However, the time needed to receive the results of the pathogen characterization phase when pathogen is not present in the patient sample or is at a concentration that is so low that culturing of the patient sample is needed. When the base test or zero culture time test shows the presence and/or concentration, the time to receive the identity and/or concentration of the pathogen can be as little as the testing time period. Accordingly, the above pathogen characterization phase can occur in a time period that is as little as the testing time period. The testing can be performed on site. For instance, since the testing can be performed using simplified robotic systems such as Proteus, the testing can occur in the same room, building, or medical complex where the patient sample was taken. As a result, the time delay associated with transportation of the patient sample to an off-site location can be removed and it becomes possible to receive the results of the pathogen characterization phase in a time period less than 30 minutes, 60 minutes, or 120 minutes.

When the pathogen characterization phase includes culturing of the patient sample, the testing schedule can begin to affect the time period needed to receive the results of the pathogen characterization phase. In the pathogen characterization phase described above, the patient sample is tested according to a testing schedule where the patient sample is sequentially tested multiple times. The time between subsequent tests is a testing interval. However, the testing schedule can be a function of the pathogen being sought and/or the type of patient sample being tested. For instance, patient samples of urine can have a testing schedule with testing at culture times of 0 minutes, 30 minutes, 60 minutes, and 90 minutes. While this testing schedule is periodic, the testing schedule need not be periodic. For instance, a patient sample of whole blood can have a testing schedule with testing at culture times of 0 minutes, 120 minutes, and 180 minutes. In some instances, the testing schedule is constructed such that the largest culture time between tests (the testing interval) can be greater than 0 minutes, 30 minutes or 60 minutes and/or less than 30 minutes, 60 minutes, or 120 minutes and/or the shortest culture time between tests (the testing interval) can be greater than 0 minutes, 30 minutes or 60 minutes and/or less than 30 minutes, 60 minutes, or 120 minutes. Additionally or alternately, the culture time limit can be a function of the pathogen being sought and/or the type of patient sample being tested. For instance, the above testing schedule show that a patient samples of urine has a culture time limit of 90 minutes and a patient samples of whole blood has a culture time limit of 180 minutes. The culture time limit is generally selected such that culturing of a patient sample having very low concentrations of a pathogen for the entire culture time limit would produce a concentration of pathogen that would be detected during testing of one of the processed samples. In some instances, the culture time limit can be greater than 0 minutes, 30 minutes or 60 minutes and/or less than 120 minutes, 180 minutes, or 240 minutes.

When the pathogen characterization phase includes culturing of the patient sample and the pathogen characterization phase provides a positive result, the results of the pathogen characterization phase can be received in a time period that is as little as the testing time period plus the testing time appointment for the test that provided positive results. For instance, when the first testing time appointment is at 30 minutes and the associated test provides a positive result, the results of the pathogen characterization phase can be received in about 60 minutes. Accordingly, when the first testing time appointment provides a positive result, the results of the pathogen characterization phase can be received in a time period greater than 60 minutes and/or less than 4 hours. When the second testing time appointment provides a positive result, the results of the pathogen characterization phase can be received in a time period greater than 90 minutes and/or less than 5 hours. When the third testing time appointment provides a positive result, the results of the pathogen characterization phase can b e received in a time period greater than 2 hours and/or less than 6 hours. When the third testing time appointment at the culture time limit provides a positive result or a negative result, the results of the pathogen characterization phase can be received in a time period greater than 2 hours and/or less than 6 hours.

In view of the above results, the pathogen identity and/or concentration can be taken into account when prescribing an antimicrobial in times as little as 90 minutes and extending up to 120 minutes, 240 minutes, or 360 minutes. The prescription can be based on guidelines that associate one or more particular antimicrobial medications with particular pathogens. Accordingly, the pathogen identity(ies) can be compared to the prescription guidelines to identify one or more antimicrobials. The comparison of the pathogen identity(ies) to the guidelines can be done manually or can be done by electronically. For instance, the guidelines can be programmed into a robotic system such as the Proteus and the robotic system can then communicate the one or more suggested antimicrobials to an operator.

Figure 2:
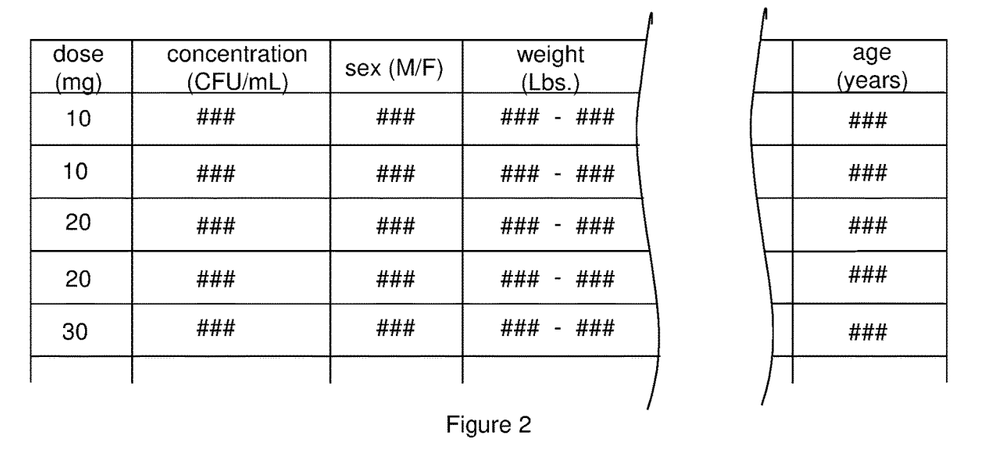
FIG. 2 is an example of dosage guidelines that associate antimicrobial dosage with one or more secondary factors.

The dosage of a prescribed antimicrobial can be a function of one or more secondary factors. For instance, FIG. 2 present an example of a table that associates dosage with secondary factors such as concentration of pathogen in the patient sample, sex, weight, and age. The table can be specific to a particular one of the identified antimicrobials. Matching the secondary factors for a patient to a row of the secondary factors in the table provides the recommended dosage.

In some instances, the patient sample can enter an antimicrobial screening phase after the pathogen characterization phase. In some instances, the antimicrobial screening phase is performed before an antimicrobial is prescribed and the results of the antimicrobial screening phase are taken into account when prescribing the antimicrobial. In an antimicrobial screening phase the susceptibility of the identified pathogen(s) to an identified antimicrobial is tested. For instance, an antibiogram can be performed on site. The results of the antibiogram can be taken into account when making the prescription. For instance, a physician, technician, or other person authorized to write prescriptions can prescribe the antimicrobial to which the identified pathogen(s) is most susceptible or can refrain from prescribing any antimicrobials when the pathogen(s) are not susceptible to any of the identified antimicrobials.

The very low Limits Of Detection (LOD) associated with the assays described above also permits an antimicrobial screening phase to be performed in a period of time that allows a prescription to be made that is both in a reasonable period of time after taking the patient sample and is based on antimicrobial susceptibility information. For instance, the patient sample can be cultured in the presence of each one of the antimicrobials that are identified as described above. A different culture can be performed for each of the identified antimicrobials. Additionally, one or more cultures can be performed for each of the identified antimicrobials. When more than one culture is performed for a single antimicrobial, the different cultures can be performed with different concentrations of antimicrobial. The susceptibility culture time is the considered to be zero minutes at the start of the culture(s).

The susceptibility cultures are each tested to characterize the susceptibility of the pathogen to the antimicrobial to which it is exposed in the susceptibility culture. For instance, growth tests can be performed on the cultures according to a susceptibility-testing schedule that lists a series of susceptibility testing appointment times where the last is the susceptibility culture time limit. At each of the susceptibility testing appointment times, the culture(s) can each be tested so as to determine the concentration of the pathogen in the culture. The growth tests can be performed as described above. For instance, the growth tests can be manually or robotically performed using an electrochemical sensor.

The characterization of the susceptibility of the pathogen to an antimicrobial can include comparing the concentration determined in each growth test to prior results to determine if growth has occurred. The concentration of the pathogen in the base test (zero culture time test) of the pathogen characterization phase can serve as the initial concentration of pathogen(s) in the patient sample. Accordingly, the concentrations determined from growth tests can be compared to the concentration determined in the base test. A significant increased concentration indicates growth of the antimicrobial. For instance, an increase in concentration of the pathogen of more than twice, triple, or quadruple over a period of at least 60 minutes, 90 minutes, or 120 minutes indicates growth of the antimicrobial. When a growth test shows that growth of antimicrobial occurs, the pathogen is characterized and reported as resistant and that result can be reported to a physician, technician or other person associated with treatment of the patient. When each of the tests in the full susceptibility testing schedule indicate that growth has not occurred, the pathogen is characterized and reported as susceptible and that result can be reported to the physician, technician or other person associated with treatment of the patient.

Figure 3:
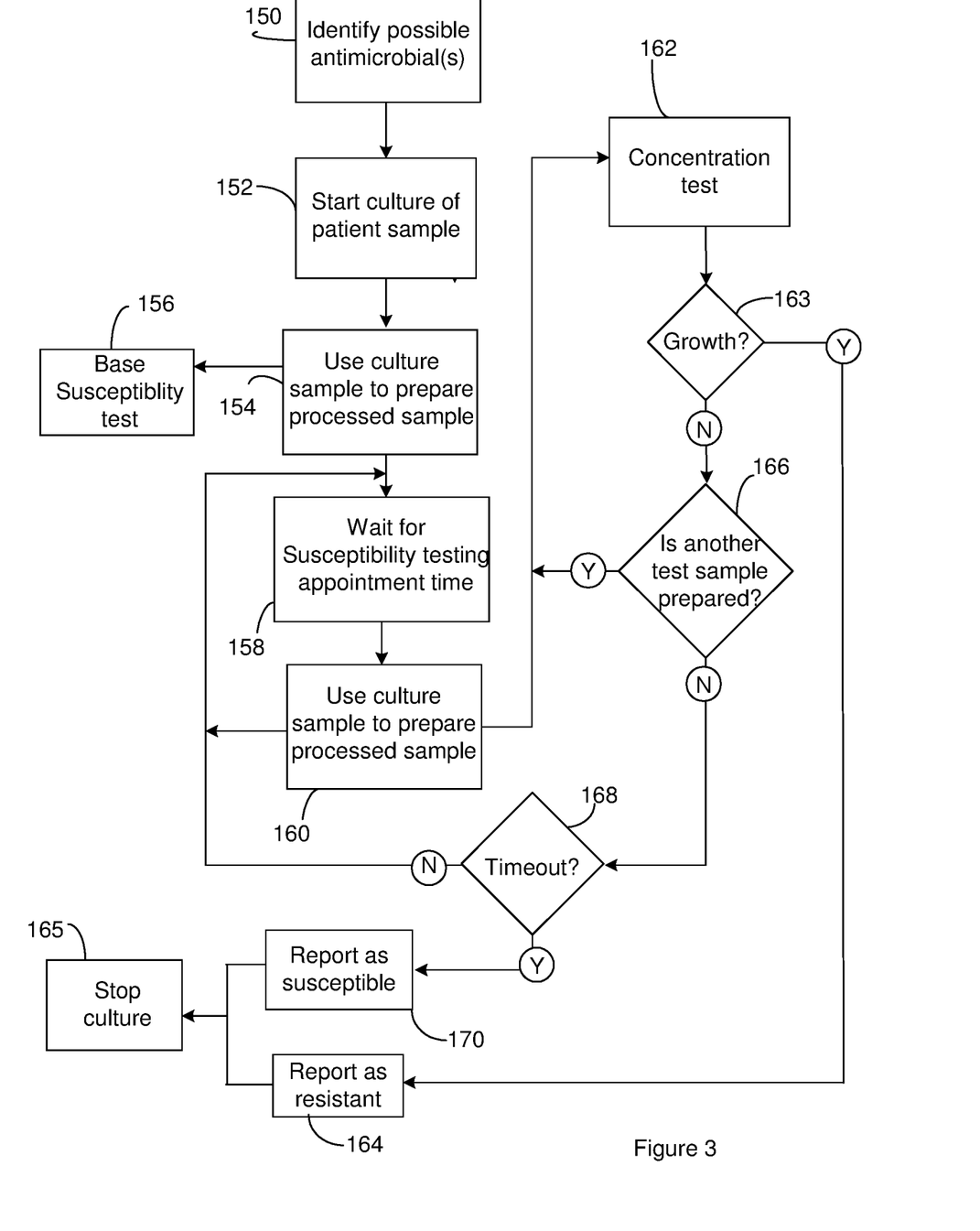
FIG. 3 is an example of a process flow of an antimicrobial screening phase.

FIG. 3 is an example of a process flow of an antimicrobial screening phase. At process block 150, one or more antimicrobials are identified that may be suitable for treating the one or more pathogens identified in the pathogen characterization phase. The one or more antimicrobials can be identified as described above. For instance, the one or more antimicrobials can be identified using guidelines that associate one or more particular antimicrobials with particular pathogens.

Susceptibility culture(s) of the patient sample taken during the pathogen identification phase are started at process block 152. As noted above, one or more susceptibility cultures are performed for each of the identified antimicrobials. A susceptibility culture for a particular antimicrobial is a culture of the pathogen in the presence of the antimicrobial. For instance, at least the patient sample, the antimicrobial, and a culture medium can be combined so as to provide a susceptibility culture medium. In some instances, the culture medium and the susceptibility culture medium are liquids. The susceptibility culture(s) are performed under condition that would cause growth of the identified pathogen in the absence of the antimicrobial. As noted above, when more than one susceptibility culture is performed for a particular antimicrobial, each of the different susceptibility cultures can be performed at a different concentration of the antimicrobial. As a result, the susceptibility of a pathogen to different concentrations of an antimicrobial can be tested.

Although the process flow can be simultaneously performed for multiple different susceptibility culture, in order to simplify this discussion, the discussion proceeds as if a single susceptibility culture is performed and tested. The susceptibility culture time is measured from the start of the culture at process block 152. The susceptibility culture time is considered to be zero minutes at the start of the susceptibility culture. In general, a susceptibility culture is considered to be started when the culture sample is heated. Accordingly, when a robotic system such as the Proteus is used to conduct the susceptibility culture, the susceptibility culture is considered to be started when the Proteus starts to heat the sample.

The susceptibility culture is used to prepare a processed sample at process block 154. As noted above, the processed sample is suitable for use in subsequent assays. For instance, when the assay is performed using an electrochemical sensor, the processed sample can be suitable for use with the electrochemical sensor. As an example, the processed sample can be in direct physical contact with the electrochemical sensor and/or can be in direct physical contact with an electrode on the electrochemical sensor. In one example, the processed sample is a drop of liquid in contact with a working electrode on the electrochemical sensor. In some instances, forming at least a portion of the processed samples includes combining one or more reagents with an aliquot of a susceptibility culture sample.

The processed sample is tested for the concentration of the one or more pathogens identified in the pathogen identification phase (process block 156). Since the test is performed shortly after starting the culturing of the patient sample, this assay can serve as the base susceptibility test or the zero susceptibility culture time test.

The susceptibility culture is tested at one or more susceptibility testing time appointments on a susceptibility-testing schedule. Upon the susceptibility culture time reaching one of the testing time appointments (process block 158), the culture sample is used to prepare a processed sample (process block 160). As noted above, the processed sample is suitable for use in subsequent assays. For instance, when the assay is performed using an electrochemical sensor, the processed sample can be suitable for use with the electrochemical sensor. As an example, the processed sample can be in direct physical contact with the electrochemical sensor and/or can be in direct physical contact with an electrode on the electrochemical sensor. In one example, the processed sample is a drop of liquid in contact with a working electrode on the electrochemical sensor. In some instances, forming at least a portion of the processed samples includes combining one or more reagents with an aliquot of a susceptibility culture sample.

The processed sample is tested for the concentration of the one or more pathogens identified in the pathogen identification phase (process block 162).

A determination is made as to whether concentration of the one or more pathogens in the processed sample can be classified as showing growth at decision block 163. For instance, the concentrations resulting from the assay at process block 162 can be compared to the concentration of the pathogen in the base susceptibility test or the zero susceptibility culture time test of the antimicrobial screening phase. It is not always necessary to directly compare concentrations. For instance, a signal generated from voltammetry of each assay can be compared to a signal generated from voltammetry of the base susceptibility test or the zero susceptibility culture time test. While an increased concentration of pathogen may be considered growth, in some instances, the pathogen is only considered to show growth when the level of increase in concentration is significant. For instance, the flow can be configured such that a pathogen is only considered to show growth when the concentration of pathogen increases by more than 50%, 100%, or 200%.

When the determination at decision block 163 is positive (classified as showing pathogen growth), the pathogen is reported as being resistant to the concentration of the antimicrobial in the susceptibility culture (process block 164) and that susceptibility culture is stopped (process block 165).

When the determination at decision block 163 is negative (classified as not showing pathogen growth) and another processed sample has been prepared from the same susceptibility culture (decision block 166), the flow returns to process block 162 and the processed sample is tested for the concentration of the pathogen(s). When the determination at decision block 163 is negative (classified as not showing pathogen growth) and another processed sample has not been prepared from the same susceptibility culture (decision block 166), the process flow moves to decision block 168. At decision block 168, a determination is made whether the susceptibility culture time currently exceeds a susceptibility culture time limit or will exceed the susceptibility culture time limit at the next susceptibility testing appointment times. When the determination at decision block 168 is positive, a timeout has occurred, a susceptible result is reported at process block 170, and the culture can optionally be stopped at process block 165.

When the determination at decision block 168 is negative, the flow has not timed out and the process flow returns to process block 158. The flow also proceeds to process block 158 from process block 160. As noted above, susceptibility culture samples are taken at one or more susceptibility testing time appointments according to a testing schedule. At process block 158, the flow waits until the next susceptibility testing time appointment is reached. As each susceptibility testing time appointment is reached, the susceptibility culture sample is used to prepare a processed sample at process block 160. The repeated cycle provided by process block 158 and process block 160 can result in a series of processed samples being generated at each of the susceptibility testing time appointments.

The assays (growth tests) in the antimicrobial screening phase can be performed using the same assays as were used in the pathogen characterization phase. For instance, the growth tests in the antimicrobial screening phase be performed manually or using a robotic system such as the Proteus from GeneFluidics, Inc. of Irwindale, Ca., USA. Additionally, the reagents used in these assays can be purchased in reagent kits such as the UtiMax and the BsiMax reagent kit from GeneFluidics, Inc. of Irwindale, Ca., USA. The "16X PID/AST Sensor Chips" are electrochemical sensors sold by GeneFluidics, Inc. of Irwindale, Ca., USA for manual or automated use with the UtiMax and the BsiMax reagent kits. As noted above, these growth tests can be performed on site.

When using a robotic system such as the Proteus is used to perform a growth test, the testing time period from the operator receiving the patient sample to receiving the results of the assay (an indication of the concentration of pathogen) is generally on the order of 30 minutes. When manually performing an assay, the testing time period from the operator receiving the patient sample to receiving the results of the assay (an indication of the concentration of pathogen) is generally on the order of 30 minutes. Accordingly, the growth tests in the antimicrobial screening phase can be performed in a testing time period greater than 60 minutes, 90 minutes or 120 minutes and/or less than 180 minutes, 240 minutes or 360 minutes.

The susceptibility-testing schedule can affect the time period required to get results from the antimicrobial screening phase. The susceptibility-testing schedule has the susceptibility culture being sequentially at a series of susceptibility testing time appointments. The time between susceptibility testing time appointments is a susceptibility-testing interval. However, the susceptibility-testing schedule can be a function of the pathogen cultured and/or the type of patient sample being tested. For instance, patient samples of urine can have a susceptibility-testing schedule with testing at culture times of 0 minutes, 30 minutes, 60 minutes, and 90 minutes. While this susceptibility-testing schedule is periodic, the susceptibility-testing schedule need not be periodic. For instance, a patient sample of whole blood can have a susceptibility-testing schedule with testing at culture times of 0 minutes, 120 minutes, and 180 minutes. In some instances, the susceptibility testing schedule is constructed such that the largest susceptibility culture time between tests (the susceptibility testing interval) can be greater than 90 minutes and/or less than 120 minutes and/or the shortest culture time between tests (the susceptibility testing interval) can be greater than 60 minutes and/or less than 120 minutes. Additionally or alternately, the susceptibility culture time limit can be a function of the pathogen being cultured and/or the type of patient sample being cultured. For instance, the above testing schedule show that a patient samples of urine has a susceptibility culture time limit of 90 minutes and a patient sample of whole blood has a susceptibility culture time limit of 180 minutes. In some instances, the susceptibility culture time limit can be greater than 30 minutes, 60 minutes, or 90 minutes and/or less than 2 hours, 3 hours, or 4 hours.

The results of the antimicrobial screening phase are available in a time period that is as little as the susceptibility testing time period plus the testing time appointment that indicated growth of the pathogen. For instance, when the first susceptibility testing time appointment is at 30 minutes and the associated test indicates pathogen growth, the results of the antimicrobial screening phase can be received in about 60 minutes. Accordingly, when the first susceptibility testing time appointment provides a positive result, the results of the antimicrobial screening phase can be received in a time period greater than 60 minutes and/or less than 90 minutes. When the second susceptibility testing time appointment provides a positive result, the results of the antimicrobial screening phase can be received in a time period greater than 0 minutes, 90 minutes and/or less than 120 minutes or 240 minutes. When the third susceptibility testing time appointment provides a positive result, the results of the antimicrobial screening phase can be received in a time period greater than 120 minutes and/or less than 150 minutes or 240 minutes. When the growth testing at the susceptibility culture time limit is performed, the results of the antimicrobial screening phase can be received in a time period greater than 0 minutes, 150 minutes and/or less than 180 minutes or 240 minutes.

When the antimicrobial screening phase and the pathogen characterization phase are both performed, the time needed to receive the results can be determined by adding the time needed to get results from the antimicrobial screening phase and the time needed to get results from the pathogen characterization phase. For instance, the time needed to receive the results of both the antimicrobial screening phase and the pathogen characterization phase can be greater than 90 minutes, 120 minutes, or 150 minutes and/or less than 4 hours, 6 hours, 7 hours, or 10 hours. These times allow for real-time treatment of patients. For instance, an antimicrobial can be selected within less than these time periods. As an example, a prescription based on data from both the antimicrobial screening phase and the pathogen characterization can be made in less than one day or even a few hours.

A prescription can be made using one, two, or three factors selected from the group consisting the pathogen identity, pathogen concentration in the patient sample, antimicrobial resistance, or antimicrobial susceptibility. In an example where all three factors are used, guidelines that associate one or more particular antimicrobial medications with particular pathogens can be used to identify one or more antimicrobials that can be used to treat the identified pathogen(s). The one or more identified antimicrobials that are reported as susceptible can then be selected for the prescription. The prescribed dosage can be a function of one or more secondary factors. As noted above, FIG. 2 present an example of a table that associates dosage with secondary factors such as concentration of pathogen in the patient sample, sex, weight, and age. Matching the secondary factors for a patient to a row of the secondary factors in the table provides the recommended dosage. This prescription process avoids the prescription of antimicrobials to which the identified pathogen is resistant and accordingly reduces the creation of additional resistance. Additionally, using the concentration of pathogen in the patient sample as a factor in determining dosage can reduce overdosing and/or underdosing and can further reduces the creation of additional resistance.

The very low Limits Of Detection (LOD) associated with the assays described above also permits the possibility of a dosage-screening phase. In the dosage-screening phase, the results of the dosage prescribed to a patient can be compared to dosage performance data and then the prescribed dosage adjusted in response to that comparison. Dosage performance data indicates the level of pathogen response that is desired for the prescribed antimicrobial and/or indicates the level of pathogen response that is tolerable for the prescribed antimicrobial. For instance, the dosage performance data can indicate the concentration of pathogen or range pathogen concentration that is desired in the patient over time.

Figure 4:
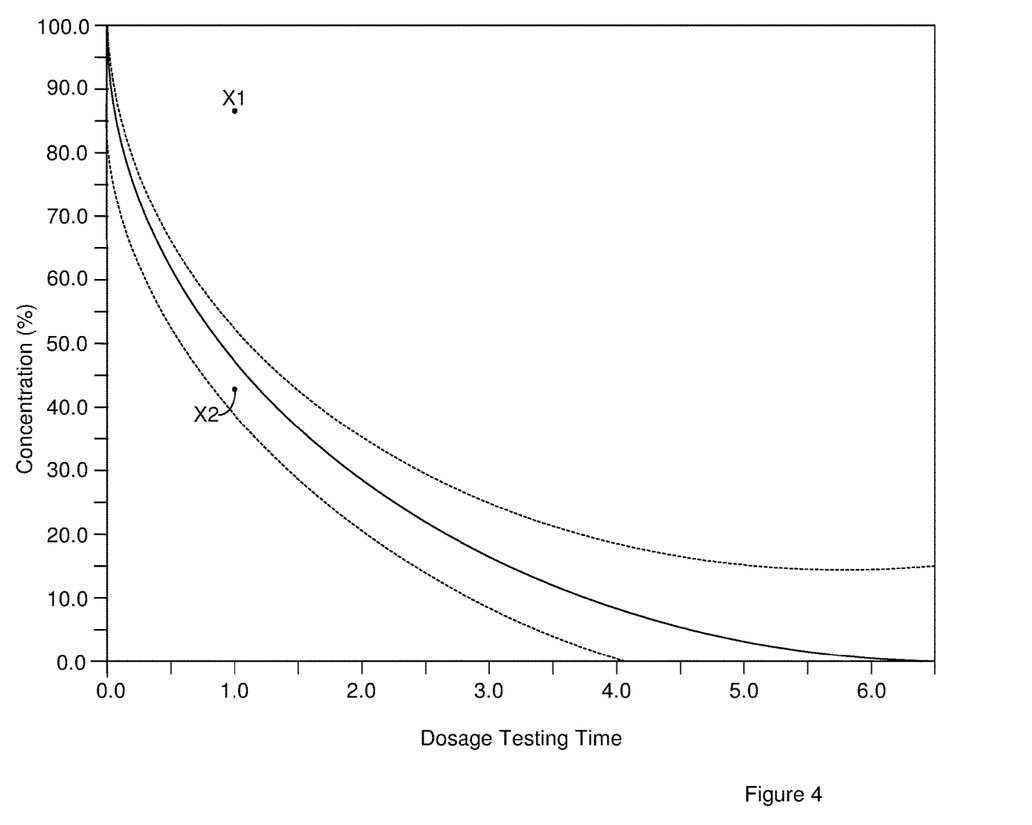
FIG. 4 is an example of dosage performance data.

FIG. 4 is an example of dosage performance data. For instance, FIG. 4 presents a generalized pathogen concentration curve that represents the concentration of pathogen in a patient's body versus dosage testing times for the situation where an antimicrobial is properly prescribed. The solid pathogen concentration curve can represent the preferred result. The dashed lines can represent the prescription tolerance. In other words, the dashed lines can represent the range of concentrations that are acceptable before changing the prescription dosage is recommended. The y-axis is the normalized concentration in that 100% represents the concentration of pathogen in the patient's body at the time the prescribed antimicrobial is first administered to the patient. The time the antimicrobial is first administered to the patient can be when the antimicrobial is first received in and/or on the patient's body. The antimicrobial can be received in or on the patient's body by injection, injection, and placement of a medium on the skin, oral administration, or nasal administration. In general, a generalized pathogen concentration curve such as is shown in FIG. 4 is specific to a particular pathogen and antimicrobial. As a result, the generalized pathogen concentration curve associated with the pathogen and antimicrobial will be used during the dosage-screening phase.

At one or more dosage testing times after an antimicrobial is prescribed, a treated patient sample can be taken that is the same type of patient sample that was previously taken. The dosage testing time is the time that the treated patient sample is taken from the patient. The treated patient sample can be tested to determine the concentration of the pathogen in the treated patient sample. When it was necessary to culture the patient sample in order to identify the presence and/or concentration of the pathogen during the pathogen characterization phase, it may be necessary to perform a culture of the treated patient sample for the same period of time as was required in the pathogen characterization phase.

The concentration of the pathogen in the treated patient sample can be normalized with the concentration of the patient sample taken during the pathogen characterization phase (i.e. concentration determined at decision block 106 of FIG. 1). The normalized concentration can then be compared to the associated generalized pathogen concentration curve such as is shown in FIG. 4. For instance, the point labeled X1 in FIG. 4 could represent the normalized concentration of a treated patient sample taken at the dosage testing times 1.0. The location of X1 above the dashed lines indicates that the prescription dosage is not providing the desired rate of decrease in the pathogen concentration. As a result, the prescription dosage can be increased in order to increase the rate of decrease in the pathogen concentration. As another example, the point labeled X2 in FIG. 4 could represent the normalized concentration of a treated patient sample taken at the dosage testing times 1.0. The location of X2 between the dashed tolerance lines indicates that the prescription dosage is providing the desired rate of decrease in the pathogen concentration. As a result, the prescription dosage can optionally be left at its current level.

Although the dosage performance data is graphically illustrated, the dosage performance data can have other formats. For instance, the dosage performance data can be in a tabular form that associates dosage testing times with a tolerance ranges for the concentration. The prescription dosage can be adjusted in response to whether the concentration of pathogen in the treated patient sample is above or below the tolerance range that is associated with the appropriate dosage testing time. The dosage performance data can have other formats such as mathematical equations such as a curve fit to one or more of the curve(s) shown in FIG. 4.

The testing of the treated patient sample can be performed as described above. For instance, the tests to determine concentration of pathogen in a treated patient sample can be performed using the same assays as were used in the pathogen characterization phase. For instance, the concentration tests in the dosage screening phase can be performed manually or using a robotic system such as the Proteus from GeneFluidics, Inc. of Irwindale, Ca., USA. Additionally, the reagents used in these assays can be purchased in reagent kits such as the UtiMax and the BsiMax reagent kit from GeneFluidics, Inc. of Irwindale, Ca., USA. The UtiMax and the BsiMax reagent kits come with electrochemical sensors that can be used manually or with a robotic system such as the Proteus from GeneFluidics, Inc. of Irwindale, Ca., USA. As noted above, these concentration tests can be performed on site.

When using a robotic system such as the Proteus is used to perform a growth test, the testing time period from the operator receiving the patient sample to receiving the results of the assay (an indication of the concentration of pathogen) is generally on the order of 25 minutes. When manually performing an assay, the testing time period from the operator receiving the patient sample to receiving the results of the assay (an indication of the concentration of pathogen) is generally on the order of 30 minutes. Accordingly, the concentration tests in the dosage-screening phase can be performed in a testing time period greater than 30 minutes, 60 minutes, or 90 minutes and/or less than 2 hours, 3 hours, or 4 hours. As a result, the prescription dosage can generally be confirmed or changed in a time period greater than 30 minutes, 60 minutes, or 90 minutes and/or less than 2 hours, 3 hours, or 4 hours.

The dosage-screening phase is described above in the context of a single treated patient sample, however, a series of treated patient samples can be taken and tested or a single treated patient samples can be taken and tested. Testing of additional treated patient samples can confirm that the prescription dosage is correct and/or can result in additional changes to the prescription dosage.

It is believed that useful results can be achieved at dosage testing times as little as 30 minutes, 60 minutes, or 90 minutes and/or less than 2 hours, 3 hours, or 4 hours. As a result, the dosage testing times in the dosage-screening phase can be hourly, daily, alternating days, skipping from 2 to 10 days between dosage testing times, bi-weekly, weekly, or monthly. Further, the dosage-screening phase can include more than 1, 2, or 3 and/or less than 4, 6, or 10 dosage testing times. Accordingly, the duration of the dosage screening phase can be greater than 20 minutes, 1 day, a week, a month, a year or can be lifelong and/or less than 30 minutes, three days, a week, month, or year.

The cultures performed during the dosage-screening phase and the pathogen characterization phase can be viability cultures. In contrast, the cultures performed during the antimicrobial screening phase need not be viability cultures. For instance, the cultures performed during the antimicrobial screening phase can be the cultures that are typically employed during antimicrobial susceptibility testing. The viability cultures increase the concentration of viable pathogen while growth of non-viable pathogen does not occur, or the concentration of the non-viable pathogen is originally so low that growth does not bring the concentration of the non-viable pathogen above a detectable level (i.e. ~1E4 CFU/mL for urine). Viable pathogen is distinguishable from non-viable pathogen because viable pathogen can be grown and multiplied in culture media where non-viable pathogen will not divide in culture media usually due to very low concentrations or undergoing stress. In contrast, cultures that are not viability cultures grow both viable pathogen and non-viable pathogen.

Example 1

A clean catch urine sample was collected from a symptomatic patient. This sample was 50 mL of unprocessed urine. One milliliters of the patient sample was manually aliquoted into a microcentrifuge tube. This tube was placed in the Proteus robotic system culture block. The Proteus automated robotic system added 1 mL of Mueller-Hinton Broth to this sample to form a liquid culture sample and to start a viability culture.

Shortly (~0 minutes) after stating the viability culture, the Proteus automated system began to prepare a processed sample from the culture sample by transferring 30 µL of the culture sample to a new microcentrifuge vial in the machine. Then, the Proteus automated system added 12 µL of 1M NaOH to the 30 µL sample. This sample was incubated at room temperature for 2 minutes. The Proteus system then added 8 µL of 1M HCl. Ten microliters of the result was placed on each of 4 sensors of the 16 available on the GeneFluidics, Inc. 16X EC chip. This chip was incubated in the Proteus machine for 11 minutes at 43° C. After completion of this incubation, the chip was washed and dried by Proteus. Ten microliters of 0.5 U/mL anti-fluorescein horseradish peroxidase (HRP) Fab fragments (Roche; diluted in 1.0% casein in 1 M phosphate-buffered saline, pH 7.4) was injected into the sensor chambers and incubated for 2 minutes at 25° C. The final reagent addition was 40 µL of 3, 3', 5, 5'-tetramethylbenzidine (TMB)-$H_2O_2$ solution (K-Blue Low Activity TMB Substrate; Neogen, Lexington Ky.) and incubated for 30 seconds to provide the processed sample.

To test the processed sample, a Helios potentiostat from GeneFluidics, Inc. was connected to the electrodes of the sensor chip and a potential of −250 mV was applied across the electrodes for one minute. During this time, the current generated by the electrochemical reaction was measured by the potentiostat. The average current measured in the final 10 seconds of the potentiostat reading constitutes the final result of the assay.

The average current signal of the four sensors reporting the assay results was 5 nA. This current level indicates a negative result with a starting concentration less than 100,000 CFU/mL $E.\ coli$. Proteus continued the culture. At a culture time of 30 minutes (corresponding to a 30 minute testing appointment time), the Proteus machine prepared a second processed sample from the culture sample using the same methodology described above for preparation of the first processed sample. The same test was run on the second processed sample and the average current signal of the four sensors reporting the assay results was 100 nA. This current level indicates a positive result with a tested concentration greater than 100,000 CFU/mL. Since the assay was specific to $E.\ coli.$, the pathogen was identified as $E.\ coli.$ As positive result was reported and the culture was stopped.

Example 2

In a hypothetical example of an antimicrobial screening phase, a local antibiogram can be used to identify antibiotics for treating the pathogen identified in Example 1. In one example, the identified antibiotics could be ciprofloxacin and imipenem. Susceptibility cultures can be started. For instance, a susceptibility culture including ciprofloxacin can be generated by diluting a portion of the patient sample to $5 \times 10^5$ CFU/mL and distributing the result into a vial with 100 µL of culture media (Mueller-Hinton broth) and 0.4 µg of a lyophilized version of the ciprofloxacin. A second susceptibility culture including imipenem can be generated by diluting a portion of the patient sample to $5 \times 10^5$ CFU/mL and distributing the result into a vial with a 0.4 µg of a lyophilized version of the imipenem and 100 µL of culture media (Mueller-Hinton broth).

The imipenem susceptibility culture sample can be used to generate an imipenem processed sample shortly after the imipenem susceptibility culture was started. The Proteus automated system can begin to prepare a processed sample from the imipenem susceptibility culture sample by transferring 30 µL of the imipenem susceptibility culture sample to a microcentrifuge vial in the machine. Then, the Proteus automated system can add 12 µL of 1M NaOH to the 30 µL sample. This sample can incubated at room temperature for 2 minutes. The Proteus system can then add 8 µL of 1M HCl. Ten microliters of the result can be placed on each of 4 sensors of the 16 available on the GeneFluidics, Inc. 16X EC chip. This chip can be incubated in the Proteus machine for 11 minutes at 43° C. After completion of this incubation, the chip can be washed and dried by Proteus. Ten microliters of 0.5 U/mL anti-fluorescein horseradish peroxidase (HRP) Fab fragments (Roche; diluted in 1.0% casein in 1 M phosphate-buffered saline, pH 7.4) can be injected into the sensor chambers and incubated for 2 minutes at 25° C. The final reagent addition can be 40 µL of 3, 3', 5, 5'-tetramethylbenzidine (TMB)-$H_2O_2$ solution (K-Blue Low Activity TMB Substrate; Neogen, Lexington Ky.) and incubated for 30 seconds to provide the imipenem processed sample.

The ciprofloxacin susceptibility culture sample can be used to generate a ciprofloxacin processed sample shortly after the ciprofloxacin susceptibility culture was started. The Proteus automated system can begin to prepare a processed sample from the ciprofloxacin susceptibility culture sample by transferring 30 µL of the ciprofloxacin susceptibility culture sample to a microcentrifuge vial in the machine. Then, the Proteus automated system can add 12 µL of 1M NaOH to the 30 µL sample. This sample can incubated at room temperature for 2 minutes. The Proteus system can then add 8 µL of 1M HCl. Ten microliters of the result can be placed on each of 4 sensors of the 16 available on the GeneFluidics, Inc. 16X EC chip. This chip can be incubated in the Proteus machine for 11 minutes at 43° C. After completion of this incubation, the chip can be washed and dried by Proteus. Ten microliters of 0.5 U/mL anti-fluorescein horseradish peroxidase (HRP) Fab fragments (Roche; diluted in 1.0% casein in 1 M phosphate-buffered saline, pH 7.4) can be injected into the sensor chambers and incubated for 2 minutes at 25° C. The final reagent addition can be 40 µL of 3, 3', 5, 5'-tetramethylbenzidine (TMB)-$H_2O_2$ solution (K-Blue Low Activity TMB Substrate; Neogen, Lexington Ky.) and incubated for 30 seconds to provide the ciprofloxacin processed sample.

The processed samples were tested for concentration using a test that served as the base susceptibility test or the zero susceptibility culture time test. For instance, a Helios potentiostat from GeneFluidics, Inc. was connected to the electrodes of the sensor chips and a potential of −250 mV was applied across the electrodes for one minute. During this time, the current generated by the electrochemical reaction was measured by the potentiostat. The average current measured in the final 10 seconds of the potentiostat reading constituted the final result of the assay. The average current signal of the four sensors reporting the assay results was 30 nA for the imipenem susceptibility culture sample and 30 nA for the ciprofloxacin susceptibility culture sample. The current levels were respectively considered to represent the concentration for the imipenem base susceptibility test and for the ciprofloxacin susceptibility base test.

The imipenem susceptibility culture and the ciprofloxacin susceptibility culture were each test according to a susceptibility-testing schedule that had susceptibility testing time appointments at 0 minutes, 60 minutes, and 90 minutes. The imipenem base susceptibility test and the ciprofloxacin susceptibility base test described above served as the test for the 0 minute susceptibility testing time appointments. The process that was used to prepare the processed samples for the base susceptibility tests was to be used to generate processed samples from each of the susceptibility cultures at 60 minutes, and 90 minutes. Each of the processed samples were tested as described above.

The test of the 60 minute imipenem processed sample provided a current of 180 nA. This result showed an increase of 500% over the current level from imipenem base susceptibility test. Accordingly, this was classified as showing growth of the $E.\ coli.$ In the presence of the imipenem. As a result, the result was reported as resistant and the imipenem susceptibility culture was stopped.

The test of the 60 minute ciprofloxacin processed sample provided a current of 30 nA. This result showed an increase of 0% over the current level from ciprofloxacin base susceptibility test. Accordingly, this processed sample was classified as showing no growth of the *E. coli*. As a result, a ciprofloxacin processed sample was also prepared at 90 minutes of ciprofloxacin susceptibility culture time. The 90 minute ciprofloxacin processed sample was tested and produced a current level that increased 0% over the current level from ciprofloxacin base susceptibility test. Accordingly, this processed sample was also classified as showing no growth of the *E. coli*. and the result was reported as susceptible to the concentration of ciprofloxacin in the ciprofloxacin culture and the ciprofloxacin susceptibility culture was stopped.

Example 3

In a hypothetical example of a dosage-screening phase a dosage of 250 mg of ciprofloxacin orally every 12 hours could be prescribed to a patient with suspected uncomplicated UTI. Twenty four hours after the first dose was administered, a patient sample of 50 mL was taken from the patient. The sample was tested for concentration of *E. coli* by using the Proteus automated system PID assay described in Example 1. The results indicated a concentration of *E. coli* was approximately 1E8 CFU/mL, which is undesirably high. As a result, the dosage was increased to 500 mg of ciprofloxacin administered orally every 12 hours. After another 24 hours a patient sample of 50 mL was taken from the patient. The sample was tested for concentration of *E. coli* by using the Proteus automated system PID assay described in Example 1. The results indicated a concentration of less than 1E4 CFU/mL in the patient sample. This result was compared to the original assay result which indicated a concentration of 1E8 CFU/mL and it was found that the concentration of *E. coli* was within acceptable levels. As a result, the treatment with ciprofloxacin was completed at a dosage of 500 mg every 12 hours.

It is believed that improvements in culture and/or assay technologies will reduce many of the times disclosed above. Accordingly, it is believed that the time needed to prescribe antimicrobials using the pathogen identity and antimicrobial susceptibility data will decrease with time. The decrease in these times will further validate the process flows set forth above.

In many of the above discussions, an assay of a cultured sample provides the concentration of a pathogen in the patient rather than the concentration of the pathogen in the culture. For instance, the concentrations on the x-axis of FIG. 4 can represent the concentration in a patient sample but, as described above, a patient sample may be cultured and the culture then tested for concentration. In order to compare the results of the test with FIG. 4, the concentration that results from the test can be converted to concentration in the patient using calibration data. For instance, calibration data can associate the concentration results after a particular culture time with concentration in the patient.

The above methods and process flows often refer to a result and/or data being reported. The reporting of data and/or results can be done to one or more entities selected from a group consisting of the patient, a physician, nurse, technician, pharmacist, person involved in treatment of the patient, or electronic device involved in the treatment of the patient. When robotic systems are used to execute the assays disclosed above, it is possible for these robotic systems to be operated by technicians or even the patient. For instance, when the dosage-screening phase does not involve culturing a patient sample, the robotic system can receive the patient sample directly from the patient or a technician, can process the sample, and provide the results to the patient or a technician. As a result, the robotic systems can be located in sites that typically include pharmacies such as CVS or Walgreens. These pharmacies can have technicians that operate the robotic systems.

The above methods and flows can be used in conjunction with patient samples such as whole blood, urine, saliva, sputum, cerebrospinal fluid (CSF), and fluid collected from bronchoalveolar lavage. Examples of pathogens that can be used with these methods and process flows include, but are not limited to, *E. coli, P. aeruginosa*, and *S. aureus*. Examples of antimicrobials that can be used with these methods and process flows include, but are not limited to, antibiotics, antivirals, and antifungals.

The above methods, process flows, and examples can be performed in a sequence other than the described sequence. Additionally or alternately, a portion of the steps, operations, flow blocks are optional. As an example, the decision block 118 and decision block 166 are optional. For instance, when the determination at decision block 108 is negative, the process flow can proceed directly to determination block 120. When the determination at decision block 163 is negative, the process flow can proceed directly to determination block 168.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:
1. A method of data application, comprising:
performing a culture of a patient sample while the patient sample is exposed to an antimicrobial candidate, the patient sample being taken from a patient, the antimicrobial candidate being a candidate for treating a pathogen in the patient sample;
performing an assay so as to identify a concentration of a pathogen in the culture; and
using the identified concentration to characterize the susceptibility of the pathogen to the antimicrobial candidate, the susceptibility of the pathogen to the antimicrobial candidate being characterized in less than 7 hours after the patient sample is taken from the patient.
2. The method of claim 1, further comprising: using the susceptibility of the pathogen to the antimicrobial candidate to identify an antimicrobial that is suitable for treating the patient.
3. The method of claim 1, wherein characterizing the susceptibility of the pathogen to the antimicrobial candidate includes determining whether the pathogen has grown during the culture.
4. The method of claim 1, wherein characterizing the susceptibility of the pathogen to the antimicrobial candidate includes comparing the identified concentration to a concentration of the pathogen in the patient sample or in a culture of the patient sample.
5. The method of claim 1, wherein the assay is one of multiple screening assays that are each performed so as to identify a concentration of a pathogen in the culture and/or in the patient sample, one or more of the screening assays being performed before the assay indicating that the has not grown in the culture.

6. The method of claim 5, wherein the screening assays each indicates that the pathogen has not grown in the culture, and
reporting the pathogen as susceptible to the antimicrobial candidate.

7. The method of claim 1, wherein the identified concentration indicates that the pathogen has grown in the culture and reporting the pathogen as resistant to the antimicrobial candidate.

8. The method of claim 1, further comprising:
performing an identification assay so as to identify a pathogen in the patient sample; and
using the identity of the pathogen in the patient sample to select the antimicrobial candidate for treatment of the patient.

9. The method of claim 8, wherein the antimicrobial candidate is selected in less than 5 hours after the patient sample is taken from the patient.

10. The method of claim 8, wherein the identification assay is performed on a processed sample generated from the patient sample, the identification assay being performed in less than 60 minutes after generation of the sample.

11. The method of claim 8, wherein the patient sample is not cultured before performing the identification assay.

12. The method of claim 11, wherein the patient sample is cultured before performing the identification assay.

13. The method of claim 8, wherein the patient sample is cultured for less than 3 minutes before performing the identification assay.

14. The method of claim 8, wherein the identification assay of the patient sample is one of multiple test assays that are sequentially performed on the patient sample, and none of the test assays performed before the identification assay assay showed that the pathogen was present in patient sample.

15. The method of claim 1, further comprising:
assaying a second patient sample taken from the patient so as to identify a concentration of the pathogen in the patient sample; and
using the identified concentration to adjust a dosage of the identified antimicribial.

* * * * *